US00PP34474P2

(12) United States Plant Patent
Smit

(10) Patent No.: US PP34,474 P2
(45) Date of Patent: Aug. 2, 2022

(54) ***PEPEROMIA* PLANT 'EC-PEPE-2111'**

(50) Latin Name: *Peperomia caperata*
Varietal Denomination: 'EC-PEPE-2111'

(71) Applicant: Eden Collection, BV, Sappemeer (NL)

(72) Inventor: Obed Smit, Sappemeer (NL)

(73) Assignee: Eden Collection B.V.

( * ) Notice: Subject to any disclaimer, the term of this patent is extended or adjusted under 35 U.S.C. 154(b) by 0 days.

(21) Appl. No.: 17/679,251

(22) Filed: Feb. 24, 2022

(51) Int. Cl.
*A01H 6/00* (2018.01)
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Cassandra Bright

(57) ABSTRACT

A new and distinct cultivar of *Peperomia* plant named 'EC-PEPE-2111' is disclosed, characterized by round, dark green leaves with deep-lying veins. Leaf upper surfaces are puckered, while the down surfaces have a red vein pattern. The new variety is a *Peperomia,* typically used as an ornamental plant.

3 Drawing Sheets

Latin name of the genus and species: *Peperomia caperata.*
Variety denomination: 'EC-PEPE-2111'.

BACKGROUND OF THE INVENTION

The new cultivar is a product of a planned breeding program to produce distinct and better performing *Peperomia* varieties. The new variety was selected as a seedling resulting from the crossing of *Peperomia caperata* 'A', and 'B', two unpatented varieties from the inventor's breeding line. The crossing was made by the inventor, Obed J. Smit, a citizen of the Netherlands in March 2018. 'EC-PEPE-2111' was selected by the inventor in 2018 at a commercial greenhouse in Sappemeer, the Netherlands.

Asexual reproduction of the new cultivar 'EC-PEPE-2111' by terminal cuttings was first performed in Sappemeer, the Netherlands at a commercial greenhouse in September 2019, and has shown that the unique features of this cultivar are stable and reproduced true to type through successive generations.

SUMMARY OF THE INVENTION

The cultivar 'EC-PEPE-2111' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-PEPE-2111'. These characteristics in combination distinguish 'EC-PEPE-2111' as a new and distinct *Peperomia* cultivar:

1. Puckered leaf surface.
2. Deep-lying veins.
3. Small, round, dark green leaves.
4. Compact, rosette-like habit.
5. Down surface of the leaves have a red vein pattern.

PARENT COMPARISON

Plants of the new cultivar 'EC-PEPE-2111' are similar to plants of the female parent, *Peperomia caperata* 'A' in most horticultural characteristics, however, plants of the new cultivar 'EC-PEPE-2111' differ from in the following characteristics:

1. Leaves of the new variety are smaller than leaves of the seed parent.
2. Leaves of the new variety are dark green on the upper side, while leaves of the seed parent are green.
3. Leaves of the new variety have a red vein pattern on the down surface, while leaves of the seed parent are light green on the down surface.

Plants of the new cultivar 'EC-PEPE-2111' are similar to plants of the male parent, *Peperomia caperata* 'B' in most horticultural characteristics, however, plants of the new cultivar 'EC-PEPE-2111' differ in the following characteristics:

1. Leaves of the new variety are more puckered with deeper-lying veins than leaves of the pollen parent.
2. Leaves of the new variety have a red vein pattern on the down surface, while leaves of the pollen parent are even red on the down surface.
3. Growth habit of the new variety is more compact than that of the pollen parent.
4. Leaves of the new variety are round, while leaves of the pollen parent are oblong with a pointed tip.

COMMERCIAL COMPARISON

Plants of the new cultivar 'EC-PEPE-2111' are similar to plants of the commercial variety *Peperomia* 'Burbella', U.S. Plant Pat. No. 32,564. However, plants of the new cultivar differ in the following characteristics:

1. Leaf upper side of the new variety is dark-green., while the leaf upper side of this comparator is grey.
2. Leaves of the new variety are smaller than leaves of this comparator.
3. Plants of the new variety are smaller than plants of this comparator.
4. Leaves of the new variety have a red vein pattern on the down surface, while leaves of this comparator are light green on the down surface; only main veins are red.

Plants of the new cultivar 'EC-PEPE-2111' are similar to plants of the commercial variety *Peperomia* 'Schumi Red', unpatented. However, plants of the new cultivar differ in the following characteristics:

1. Leaves of the new variety are round, while leaves of this comparator are oblong with a pointed tip.
2. Leaf upper side of the new variety is dark-green, while leaf upper side of this comparator is red.
3. Leaves of the new variety are more puckered with deeper-lying veins than leaves of this comparator.

BRIEF DESCRIPTION OF THE PHOTOGRAPHS

The accompanying photograph in FIG. 1 illustrates in full color a typical blooming plant of 'EC-PEPE-2111' grown in a greenhouse. The plant is approximately 30 weeks of age.

Figure 1:
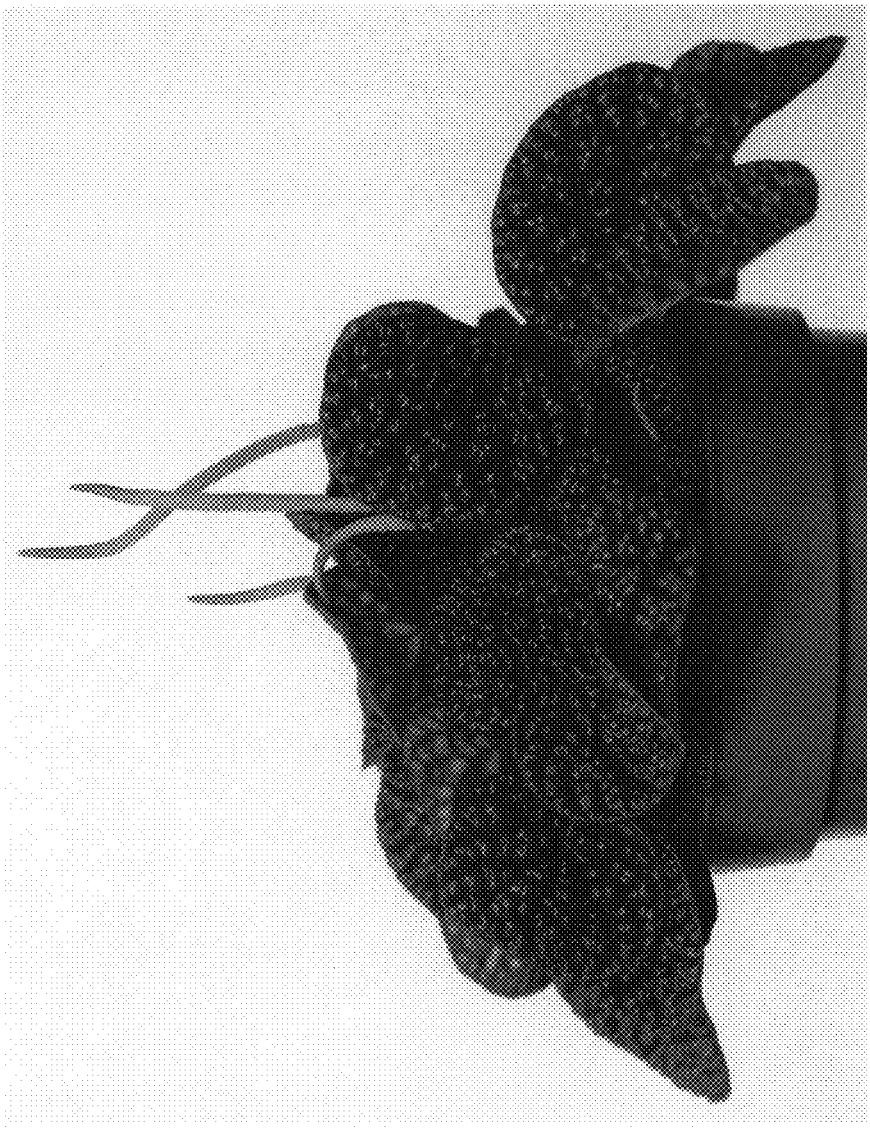
Figure 2:
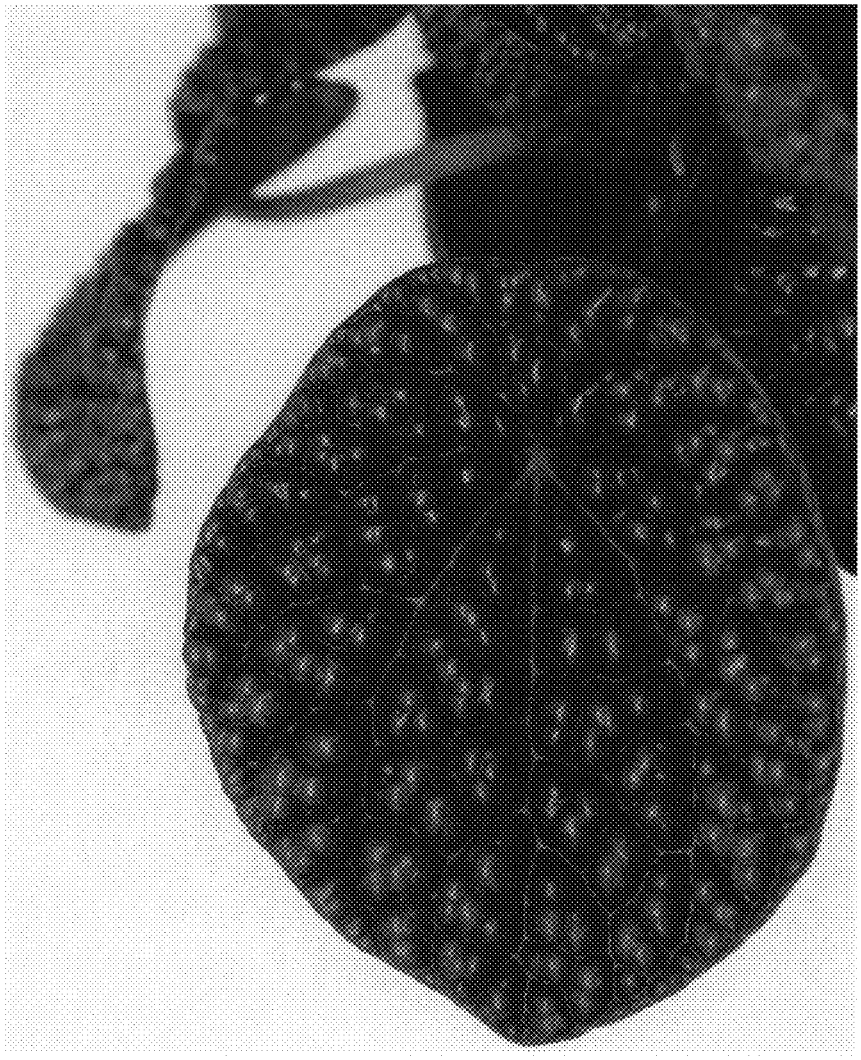
FIG. 2 illustrates a close up of the foliage.
Figure 3:
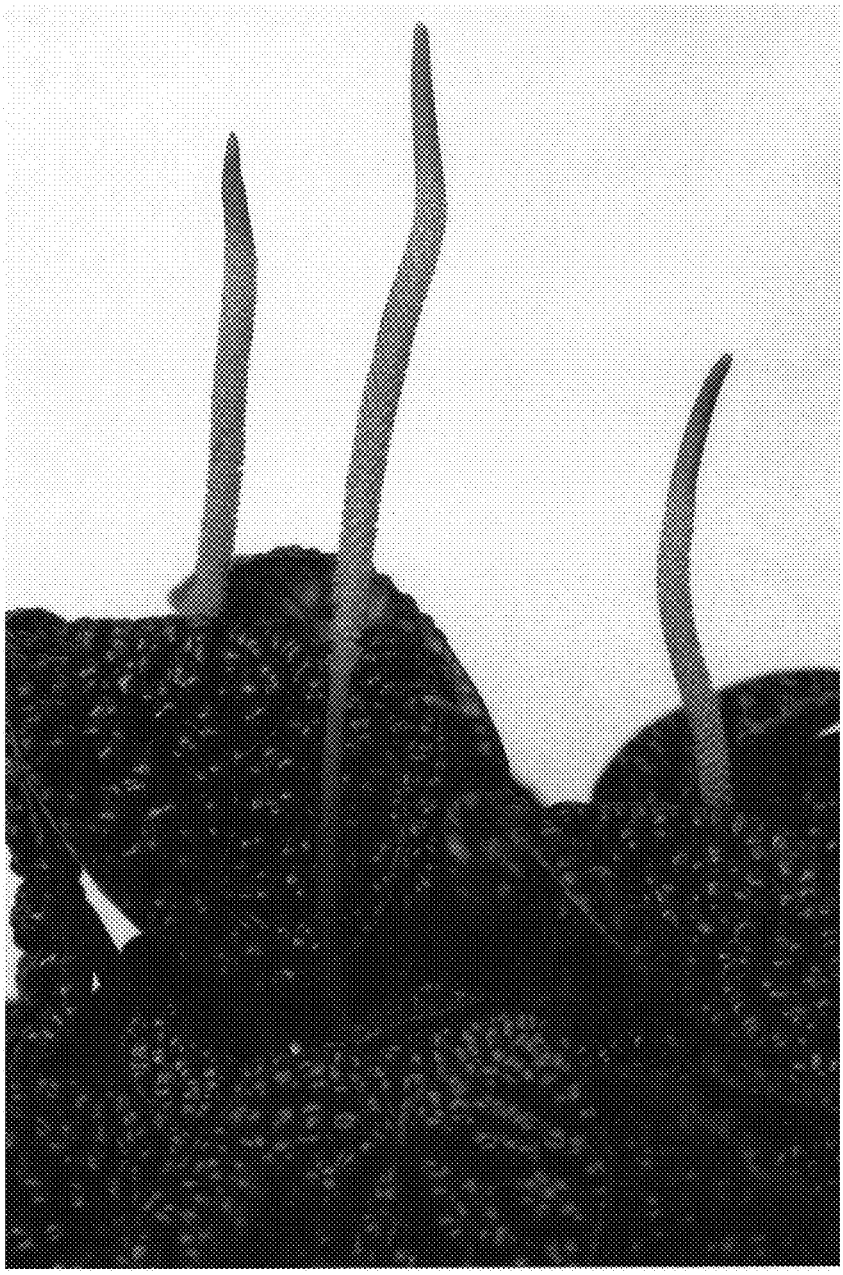
FIG. 3 illustrates a typical inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'EC-PEPE-2111' plants at 10 months of age, grown in a greenhouse in Sappemeer, the Netherlands during October. The growing temperature ranged from 18° C. to 20° C. at night to 20° C. to 22° C. during the day. Measurements and numerical values represent averages of typical flowering types.

Botanical classification: *Peperomia caperata* 'EC-PEPE-2111'.

PROPAGATION

Time to initiate roots: About 21 days at approximately 21° C. in summer.

Time to produce rooted cutting: About 28 days at 21° C. in summer.

Description of roots: Fibrous, fine, moderately dense, freely branching. White in color, not accurately measured with RHS chart.

PLANT

Plant type: Perennial potted plant.

Plant shape: Flattened globular with inflorescences carried slightly above foliar plane.

Growth habit: Rosettes of leaves, eventually forming very short, thick stems.

Plant spread: Approximately 19.4 cm.

Height: 7.5 cm to top of foliar plane; 14.4 cm to top of floral plane.

Growth rate: Moderate.

Plant vigor: Moderate.

Age of plant described: Approximately 8 months.

Branching habit: Leaves in rosettes, eventually forming very short, thick stems, branching into lateral rosettes of leaves.

Pinching: Pinching not required.

Number of primary (main) branches per plant: Average 4.

Number of secondary (lateral) branches per plant: Average 3.

Main branches:

*Length.*—Average: 1.5 cm.

*Diameter.*—Average: 0.5 cm.

Internode length: Average: Less than 0.1 cm.

Appearance and shape: Succulent, thick and rounded.

Luster: Matte.

Aspect/angle from vertical: Average angle: 20°.

Strength: Moderately strong.

Color:

*Developing.*—RHS Yellow-Green 146A.

*Mature.*—RHS Yellow-Green 146A.

*At internodes.*—RHS Yellow-Green 146A.

Pubescence: None.

Plant fragrance: None.

FOLIAGE

Leaf:

*Arrangement.*—Alternate, single.

*Quantity.*—Average 12.

*Average length.*—3.9 cm.

*Average width.*—3.5 cm.

*Shape of blade.*—Broad ovate to cordate, perfoliate.

*Apex.*—Broad bluntly acute to near obtuse.

*Base.*—Truncate to shallow cordate, lobes connected and forming a perfoliate leaf.

*Margin.*—Entire, slightly revolute.

*Texture of top surface.*—Glabrous, smooth, moderately leathery, strongly bullate.

*Texture of bottom surface.*—Glabrous, smooth, moderately leathery.

*Pubescence.*—None.

*Luster, upper side.*—Glossy.

*Luster, under side.*—Matte, velvety.

*Color.*—Young foliage upper side: RHS Yellow-Green 144B, veined Greyed-Orange 174A. Young foliage under side: RHS Yellow-Green N148D, veined 152C. Mature foliage upper side: RHS Green 137A, area surrounding veins Green 139A to Yellow-Green 147A, but darker. Mature foliage under side: RHS Yellow-Green 147D.

*Venation.*—Pattern: Parallel, strongly furrowed. Venation color upper side: RHS Greyed-Green 191B. Venation color under side: RHS Greyed-Red 180A.

*Petiole.*—Average Length: 6.7 cm. Diameter: 0.3 cm. Texture: Glabrous, smooth. Luster: Both sides slightly glossy. Strength: Low. Color, upper side: RHS Yellow-Green N148B, moderately finely-striped Greyed-Red 182A, more densely toward distal end. Color, under side: RHS Yellow-Green N148B, moderately finely-striped Greyed-Red 182A, more densely toward distal end.

FLOWER

Inflorescence:

*Arrangement.*—Axillary spike.

*Inflorescence type and form.*—Spike.

*Inflorescence height.*—Average: 7.2 cm (excluding peduncle).

*Inflorescence diameter.*—Average: 0.3 cm.

*Quantity of flowers per inflorescence.*—Average 700 individual flowers per spike.

*Quantity of flowers per plant.*—Average 3,000.

*Quantity of flower buds per plant.*—Average 3,300.

*Quantity of flowers and buds per plant.*—Average 6,300.

*Natural flowering season.*—Fall into late spring.

Flower bud:

*Flower bud length.*—0.2 mm.

*Flower bud diameter.*—0.2 mm.

*Flower bud shape.*—Flattened, circular.

*Flower bud texture.*—Glabrous, smooth, slightly velvety.

*Flower bud luster.*—Slightly glossy.

*Flower bud color.*—Near RHS Yellow-Green 148C, tinged near Greyed-Purple 185A.

Flower:

*Flower type and form.*—Individual flowers are very small and consist of 1 bract, 2 stamens and a single pistil.

*Flower aspect.*—Outward.

*Flowering habit.*—Very freely.

*Fragrance.*—None.

*Flower shape.*—Rotate, consisting of 1 bract, 2 stamens and 1 pistil only; no petals and sepals present.

*Flower height.*—Average: 0.6 mm.

*Flower diameter.*—Average: 0.5 mm.

*Flower length.*—Average: 0.7 mm.

*Flower longevity on plant.*—Average one month.

*Persistent of self-cleaning.*—Self-cleaning.

Peduncles:

*Terminal peduncle length.*—Average 6.6 cm.

*Terminal peduncle diameter.*—Average 2.0 mm.

*Peduncle angle to lateral branch axis.*—Average angle 30°.

*Peduncle strength.*—Weak.

*Peduncle texture.*—Glabrous, smooth.

*Peduncle luster.*—Moderately glossy.

*Peduncle color.*—RHS Yellow-green 148D, slightly finely-striped Greyed-Red 181C.

Floral bracts:

*Quantity per flower.*—One below each individual flower.

*Shape.*—Orbicular.

*Length.*—0.4 mm.

*Width.*—0.4 mm.

*Color.*—Near RHS Yellow-Green 147B, slightly tinged near Greyed-Purple 185A.

REPRODUCTIVE ORGANS

Stamens:

*Number.*—Average 2.

*Filament length.*—Average 0.3 mm.

*Filament color.*—Near RHS Yellow-Green group, impossible to measure due to small size.

Anther:

*Shape.*—Ovate.

*Length.*—Average 0.3 mm.

*Width.*—Average 0.15 mm.

*Color.*—Near RHS Green-White 157D or lighter.

*Pollen.*—Low.

*Pollen color.*—RHS White 155A.

*Pistil.*—Number: Average 1. Length: Average 0.5 mm.

*Stigma.*—Shape: Flattened, hairy, circular. Length: Average 0.1 mm. Diameter: Average 0.3 mm. Color: Near RHS Yellow-Green N148D. Style: Sessile. Ovary color: Near RHS Yellow-Green 147C.

OTHER CHARACTERISTICS

Seeds and fruits: None observed to date.

Disease/pest resistance: No increased nor decreased resistance nor susceptibility to normal diseases and pests of *Peperomia* has been observed.

Temperature tolerance: Tolerates temperatures up to 40° C. Hardy to USDA zones 10 to 12.

What is claimed is:

1. A new and distinct cultivar of *Peperomia* plant named 'EC-PEPE-2111' as herein illustrated and described.

* * * * *